United States Patent
Johnnie et al.

(10) Patent No.: US 8,483,977 B1
(45) Date of Patent: Jul. 9, 2013

(54) METHOD OF LASER VIBRATION DEFECT ANALYSIS

(75) Inventors: Nathan Johnnie, Middletown, RI (US); Lynn T. Antonelli, Cranston, RI (US); Francis J. O'Brien, Jr., Newport, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 491 days.

(21) Appl. No.: 12/794,065

(22) Filed: Jun. 4, 2010

(51) Int. Cl.
*G01B 5/28* (2006.01)

(52) U.S. Cl.
USPC .......................................................... 702/36

(58) Field of Classification Search
USPC ............................................. 702/36; 73/657
See application file for complete search history.

(56) References Cited

U.S. PATENT DOCUMENTS

| | | | |
|---|---|---|---|
| 5,505,090 A * | 4/1996 | Webster | 73/657 |
| 7,277,573 B1 * | 10/2007 | O'Brien, Jr. | 382/154 |
| 8,009,209 B2 * | 8/2011 | Chapman et al. | 348/246 |
| 2004/0176210 A1 * | 9/2004 | Narai et al. | 476/73 |

* cited by examiner

*Primary Examiner* — Tung S Lau
*Assistant Examiner* — Xiuquin Sun
(74) *Attorney, Agent, or Firm* — James M. Kasischke; Michael P. Stanley; Jean-Paul A. Nasser (57) ABSTRACT

A method for locating defects in a target includes subjecting the target to an ultrasonic vibration. A first laser beam is then transmitted to the target and a reflection is received. A vibration signal is produced from the reflection that gives the target's response to the ultrasonic vibration. A digital image is produced of the target that includes the region of the first laser beam reflection. The digital images are overlaid with the vibration signal to provide overlaid data. The overlaid data is tested to determine a probability of the overlaid data being non-random. The probability is compared against a threshold to indicate a potential area of concern that may include defects.

4 Claims, 3 Drawing Sheets

METHOD OF LASER VIBRATION DEFECT ANALYSIS

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION

1. Field of the Invention

The present invention relates generally to a laser measurement tool that measures vibrations at locations of interest in response to an ultrasonic operator and, more particularly, provides useful information with large sample rates in highly dynamic vibration noisy environments and/or relatively solid structures.

2. Description of the Prior Art

According to a report released in 2005 by the American Society of Civil Engineers (ASCE), a total of about 160,570 bridges, or just over one-quarter of the nation's approximately 590,750-bridge inventory, were rated structurally deficient or functionally obsolete. The basic cause of failure is metal fatigue brought on by many possible intermediate causes. Every State has a large number of bridges. For example, Rhode Island has about 753 bridges, California has about 24,028 bridges, and Texas has about 49,504 bridges. Bridges, like any fabricated structure, can fail for many reasons. Prevention of such failures is of paramount importance.

Many patents attempt to detect structural failures by a general method called Structural Health Monitoring (SHM), a methodology that involves the placement of sensors inside a structure, which can communicate structural status to inspectors. However, the location of the sensor(s) is problematic. For example, a crack could form almost any place in a gusset plate. Moreover, when a fatigue crack becomes visible, only a small percentage of the life remains, perhaps as little as about 10%. The likely list of causes for bridge disasters include the following: fatigue cracks, corroded gusset plates, frozen bearings, overweight construction materials, weather, de-icing materials, and an unstable bridge deck.

It is highly desirable that new technologies be available to local, state and federal agencies for quickly scanning a large number of bridges to locate any failure points to avoid potentially devastating disasters.

The following U.S. Patents describe various prior art systems that may be related to the above and/or other problems:

U.S. Pat. No. 7,286,964, issued Oct. 23, 2007, to Kim, discloses methods and recordable media for monitoring structural health conditions. A method is disclosed for interrogating for damage of a host structure using a diagnostic network patch (DNP) system having patches. An interrogation module partitions the plurality of patches in subgroups and measures the sensor signals generated and received by actuator and sensor patches, respectively. Then, a process module loads sensor signal data to identify wave modes, determine the time of arrival of the modes and generate a tomographic image. It also determines distribution of other structural condition indices to generate tomographic images of the host structure. A set of tomographic images can be stacked to generate a hyperspectral tomography cube. A classification module generates a codebook based on K-mean/Learning Vector Quantization algorithm and uses a neural-fuzzy-inference system to determine the type of damages of the host structure.

U.S. Pat. No. 7,281,428, issued Oct. 16, 2007, to Kim, discloses interrogation systems for monitoring structural health conditions. An interrogation system includes at least one wave generator for generating a wave signal and optical fiber sensors applied to a structure. The interrogation system also includes at least one electronic module for generating an input sensor signal and sending the input sensor signal to the optical fiber sensors. Each optical fiber sensor impresses the wave signal onto the input sensor signal to generate an output sensor signal that is frequency shifted from the input sensor signal. The electronic module generates an information signal in response to the output sensor signal. The interrogation system also includes a signal processing unit and a relay switch array module that has relay switches. Each relay switch relays the information signal to the signal processing unit and the signal processing unit generates a digital sensor signal that is subsequently sent to a computer.

U.S. Pat. No. 7,277,573, issued Oct. 2, 2007, to O'Brien, Jr., which is incorporated herein by reference, discloses a multi-stage method for automatically characterizing data sets containing data points which are each defined by measurements of three variables as either random or non-random. A three-dimensional Cartesian volume which is sized to contain all of a total number N of data points in the data set which is to be characterized. The Cartesian volume is partitioned into equal sized cubes, wherein each cube may or may not contain a data point. A predetermined route is defined that goes through every cube one time and scores each cube as a one or a zero thereby producing a stream of ones and zeros. The number of runs is counted and utilized to provide a Runs Test, which predicts if the N data points in any data set are random or nonrandom. Additional tests are used in conjunction with the Runs Test to increase the accuracy of characterization of each data set as random or nonrandom.

U.S. Pat. No. 7,267,008, issued Sep. 11, 2007, to Gordon et al, discloses a transducer for use in a structural health monitoring system that includes a single transducer element. The transducer includes a transmit assembly coupled to the single transducer element. This assembly is configured to produce a multi-cycle square wave drive signal for stimulating the transducer. Additionally, a transmit/receive switch coupled to the single transducer element is provided. This assembly is configured to isolate the drive signal from the receive assembly used to sense the electrical signal generated from any received elastic waves.

U.S. Pat. No. 7,246,521, issued Jul. 24, 2007, U.S. Pat. No. 7,197,931, issued Apr. 3, 2007, and U.S. Pat. No. 7,117,742, issued Oct. 10, 2006, to Kim, disclose sensors and systems for monitoring structural health conditions. A device is provided for monitoring structural health conditions including a dielectric substrate, a piezoelectric device for actuating and/or sensing waves, a molding layer deposited over the piezoelectric device, a cover layer deposited over the molding layer and a hoop layer surrounding the piezoelectric device and being attached to the substrate. The device further includes an optical fiber coil sensor attached to the dielectric substrate, where the coil sensor has a rolled optical fiber cable and a coating layer applied to the rolled optical fiber cable. A diagnostic patch network includes a plurality of patch sensors attached to a host structure and a bridge box connected to the patch sensors. The bridge box sends information of structural health conditions to and receives power from a ground control system using a wireless communication technique.

U.S. Pat. No. 7,080,555, issued Jul. 25, 2006, to Austin et al, discloses a distributed real time health monitoring system for monitoring of acoustic emission signals from different regions of a structure such as aircraft or spacecraft structures. The health monitoring system has its analysis and prognosis intelligence distributed out to the local regions being monitored and therefore does not require extensive cabling systems to carry the high bandwidth information characteristic of acoustic emission.

U.S. Pat. No. 7,075,424, issued Jul. 11, 2006, to Sundaresan et al, discloses a sensor array for non-destructively monitoring a structure to detect a critical structural event. The sensor array includes a plurality of discrete sensor nodes, each of the discrete sensor nodes producing an electrical signal in response to a structural event. A signal adder is electrically connected to the plurality of discrete sensor nodes for receiving and combining the electrical signal from each of the discrete sensor nodes to form a single sensor array output signal. A signal processing module then receives and processes the single sensor output signal. In the preferred embodiment, the signal processing module uses the time interval between the electrical signals from each of the discrete sensor nodes formed into a single sensor array output signal to calculate the location of the critical structural event. Also, in the preferred embodiment, a data collection system is located downstream of the sensor processing module.

U.S. Pat. No. 6,826,982, issued Dec. 7, 2004, to O'Brien et al, which is incorporated herein by reference, discloses a method and apparatus for detecting and monitoring fractures in a structure by monitoring acoustic energy transmitted within the structure by receiving continuously over a period of time electrical signals from a plurality of acoustic transducers carried by the structure in a pulse processor to form data bursts from pulses in the signals and deriving, for each of a plurality of the data bursts, delta-t values representing the differences between burst arrival times at each sensor, the delta-t values forming a delta-t pattern, and generating a damage indication signal when the delta-t pattern is repeated to a predetermined degree.

U.S. Pat. No. 6,399,939, issued Jun. 4, 2002, to Sundaresan et al, discloses a sensor array for nondestructively monitoring a structure to detect a critical event. The sensor array includes a plurality of discrete sensor nodes, each of the discrete sensor nodes producing an electrical signal in response to a structural event. In the preferred embodiment, the sensor nodes include a plurality of piezoceramic fibers arranged in a planar array in which the fibers are aligned substantially parallel to each other, each of the fibers having a plurality of polarized regions that are substantially oriented according to their polarity in either a series, parallel, or combined arrangement of series and parallel orientations, and an electrical interface connecting the plurality of polarized regions of each fiber in series with one another. A signal adder receives and combines the electrical signals from each of the discrete sensor nodes to form a single sensor array output signal. In the preferred embodiment, the electrical interface further includes at least one electrical bus substantially aligned with the fibers and a signal processing module for receiving and processing the single sensor output signal. The signal processing module is linked through the digital data bus to a central processing unit. The plurality of discrete sensor nodes may further be divided into discrete subgroups, each located at a different structural location to provide a degree of sensing and determining the location of the structural event. In the preferred embodiment, the discrete sensor nodes are electrically connected in series, thereby forming a continuous series connection between each of the discrete sensor nodes to improve the likelihood that a critical structural event will be detected.

U.S. Pat. No. 5,505,090, issued Apr. 9, 1996, to Webster, discloses an apparatus for non-destructively inspecting for faults in or beneath the surface of structures, such as debonds or delaminations in composite materials, or cracks, broken stringers, delaminations and the like in semi-monocoque structures, which includes at least one spark gap discharge device displaced from the test object which focuses an acoustic pulse onto a small local area of the object for vibrationally exciting the surface of that area. A laser Doppler camera system, also displaced from the test object directs a laser beam onto the excited area and derives from light energy reflected back from the excited area the velocity of out-of-surface displacement of, and relaxation frequencies generated by, the surface of the excited area and provides an indication of whether a fault is present in that area. Acoustic pulses and the laser beam are directed to successive local areas in synchronism according to a scanning pattern, at each of which the reflected light energy is analyzed, following which the acquired data is processed and visually displayed in a manner which clearly indicates the presence of a fault and its location and enables the operator to further analyze the data to ascertain the type and extent of the fault.

The article "Model for continuously scanning ultrasound vibrometer sensing displacements of randomly rough vibrating surfaces," by Ratilal et al., from the Journal of Acoustical Society of America, February 2007, 0001-4966/2007/121(2)/863/16, discloses an analytic model for the time-dependent ultrasound field reflected of a randomly rough vibrating surface for a continuously scanning ultrasound vibrometer system in bistatic configuration. The model incorporates the beam patterns of both the transmitting and the receiving ultrasound transducers and the statistical properties of the rough surface. Motions of the vibrometer over the randomly rough surface leads to time dependent scattering noise that causes a randomization of the received signal spectrum. Simulations with the model indicate that the surface displacement and velocity estimation are highly dependent upon the scan velocity and projected wavelength of the ultrasound vibrometer relative to the roughness height standard deviation and correlation length scales of the rough surface. The model is applied to determine limiting scan speeds for ultrasound vibrometer measuring ground displacements arising from acoustic or seismic excitation to be used in acoustic landmine confirmation sensing.

The above cited prior art does not disclose a laser vibration analyzer which provides useful large sample size measurements involved in scanning structures carried out in the dynamic environment of nature, which includes the presence of vibrations, background noise, traffic noise, transformer noise, engine (machinery) noise, seismic noise, and other interferences inherent when making measurements in the real world including during operation. The solutions to the above described and/or related problems have been long sought without success. Consequently, those skilled in the art will appreciate the present invention that addresses the above and other problems.

SUMMARY OF THE INVENTION

It is a general purpose of the present invention to provide an improved laser measurement tool.

One possible object of the present invention is to provide a laser measurement tool that can be utilized to scan a target, which may include solid structures, to produce large samples of vibrations of interest to aid in the detection of structural material faults in a highly dynamic environment, e.g., a noisy environment.

These and other objects, features, and advantages of the present invention will become apparent from the drawings, the descriptions given herein, and the appended claims. However, it will be understood that the above listed objects and advantages of the invention are intended only as an aid in understanding certain aspects of the invention, are not intended to limit the invention in any way, and do not form a comprehensive or exclusive list of objects, features, and advantages.

Accordingly, the present invention provides a laser vibration analyzer for use in a noisy environment at a distance offset from a target. The laser vibration analyzer may comprise an ultrasonic transmitter operable to transmit an ultrasonic signal to the target and an ultra receiver operable to detect a reflected ultrasonic signal from the target. A laser vibrometer transmitter/receiver is operable to produce a vibration signal responsive to vibrations produced in the target by the ultrasonic signal. A camera produces digital images of the target. A signal stabilizer removes extra pulses in the digital images produced by noise other than the ultrasonic signal. A processor overlays the digital images of the target with the vibration signal to provide overlaid data. A noise discrimination filter utilizes a selected probability to predict whether data points of the overlaid data is random or non-random. The probability provides an indication of a possible structural defect.

The laser vibration analyzer may further comprise a laser listening device operable to produce an audio signal in response to the vibrations produced in the target by the ultrasonic signal sound generator. An adder is operable to add the filtered audio signal to the digital images, and a switch is operable to selectively connect the filtered audio signal with the adder. In one embodiment, the laser listening device comprises an infrared laser and detector.

In another embodiment, the present invention provides a method for analyzing vibrations for use in a noisy environment at a distance offset from a target. The method may comprise steps such as transmitting an ultrasonic signal to the target, transmitting a first laser beam to the target, receiving a first reflection of the first laser beam, and producing a vibration signal from the first reflection of the first laser beam responsive to vibrations produced in the target by the ultrasonic signal. Other steps may comprise producing digital images of the target, removing noise from the digital images produced by noise other than the ultrasonic signal, and overlaying the digital images of the target with the vibration signal to provide data points of overlaid data. The method may further comprise determining a probability of the data points of the overlaid data being random data points and non-random. The probability provides an indication of a possible structural defect.

The method may further comprise transmitting a second laser to the target, detecting a second reflection from the second laser, and producing an audio signal in response to the vibrations produced in the target by the ultrasonic transmitter. The method may further comprise utilizing an infrared laser for the second laser.

The method may further comprise frequency filtering the audio signal to produce a filtered audio signal, and utilizing a switch to selectively add the filtered audio signal to the digital images.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings, wherein like reference numerals refer to like parts and wherein.

DETAILED DESCRIPTION OF THE INVENTION

Figure 1:
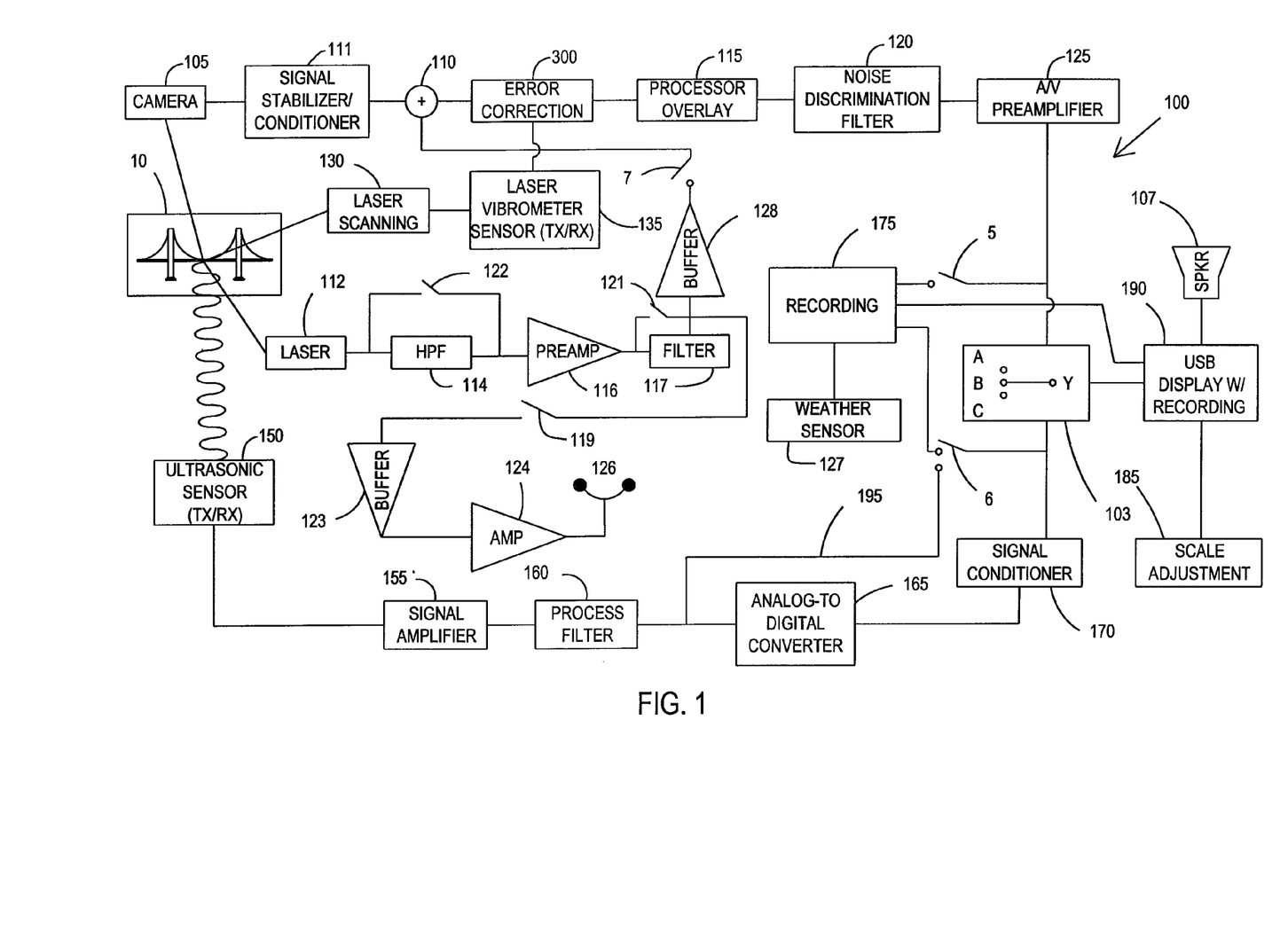
FIG. 1 is a schematic functional block diagram for a laser vibration analyzer in accord with one possible embodiment of the present invention.

Referring now to the drawings and, more particularly, to FIG. 1, there is shown a functional block diagram for laser vibration analyzer 100, which provides a general overview of the inventive device and method.

One presently preferred embodiment of laser vibration analyzer 100 may comprise several input processing nodes or sections. These nodes may generally correspond with functional blocks such as digital camera 105, laser vibrometer sensor 135, scanning laser 130, ultrasonic sensor 150, and laser transmitter and receiver 112.

Target 10 is shown as a bridge but may be a wide range of different targets. Laser vibration analyzer 100 has unlimited usage whether it is used for civilian, medical, or military applications. Many different types of structures may be analyzed. As one example, the present invention is not limited to, for example, monocoque or semi-monocoque structure, as some prior art laser vibrometer systems are. The present invention may be utilized to gather large samples of dynamic measurements while the structure is in use. For example, the present invention would not require shutting down bridges for testing but could be utilized while the bridges are in use.

The present invention provides a unique way to streamline data collection and analysis by means of a novel three-dimensional spatial randomness assessment tool. In one possible embodiment, application of this tool and providing pre-processing filtering steps assures the probable success of the task. A noise discrimination tool, as well as other significant features described hereinafter, assures that the integrity of laser vibration analyzer 100 is not compromised by the presence of vibrations, background noise, traffic noise, transformer noise, engine (machinery) noise, seismic noise, and other interferences inherent in the large-sample task carried out in the dynamic environment of nature. Laser vibration analyzer 100 accounts for dynamic conditions such as these and takes into account the associated structural and environmental variables of vibration, noise, and video signal stabilization constraints. The output of laser vibration analyzer can be either a position, a velocity or an acceleration.

Camera 105 is preferably a digital high resolution camera that is utilized while mapping an area of interest. Camera 105 is used in conjunction with scanning laser 130 and laser vibrometer sensor 135 and can provide that the digital camera images are at the same position as the position being scanned by scanning laser 130. The produced digital images can also be utilized to help the investigator to pinpoint the location or locations that require attention.

Scanning laser 130 is joined to laser vibrometer sensor 135 for detecting a vibrational signal from the position being scanned. This vibrational signal is typically a velocity measurement obtained by Doppler analysis of the reflected laser beam from scanning laser 130. Other methods can be used such as by using return times for measuring a positional difference between the scanning laser 130 and the position at two different times. The change in position over time can be used to give velocity. Another variation would include using well known techniques to obtain the acceleration at the position. Any of these methods could work for obtaining a vibrational signal. The scanning laser 130 also allows calculation of the coordinates of the position being scanned.

Scanning laser 130 and laser vibrometer sensor 135 are a laser Doppler vibrometer used to focus a continuous laser beam onto a point on the structure, e.g. target 10, to be measured. The reflection from the structure can be processed with a commercial Doppler interferometer to provide a measure of the velocity of the structure along the axis of the laser beam. The laser beam can be scanned across the structure at distances up to 300 meters. The scan points can be preselected or selected in real time by the sensor system operator. As discussed hereinbefore, the laser scan locations can be identified relative to the image of the structure obtained from the camera 105.

Different types of laser Doppler vibrometers can be used depending on the desired need. In one embodiment, the laser vibrometer may utilize infrared light, which is not affected by weather conditions such as clouds or fog.

Laser scanning speed control 130 is adjustable. It is designed to compensate for the scanner movement whether the system is dynamic or static to ensure the system collects correct readings of the scanned area. The scanning may be continuously swept over the target or may proceed in a stepped manner where selected points on the target are sequentially scanned.

Each laser scan point signal acquisition is also synchronously timed to the ultrasound acoustic pulses produced by ultrasonic sensor 150. As with many transducers, ultrasonic sensor 150 is capable of both transmitting and receiving acoustic energy. The reaction of target 10 to the ultrasound pulses may be measured by the laser at a series of particular points on the structure. A modal pattern of the structure motion can be generated by combining the signals recorded by the laser sensor at different points on the structure, which may be utilized for detecting hot spots.

Ultrasonic sensor 150 produces waves that penetrate objects subjected to vibration analyses due to design flaws or natural structure problems in order to determine the degree of stability and any inherited risks that could cause degradation to safety and/or occasionally cause fatalities or monetary losses. The device can be used for other purposes, e.g., to expose bunkers or tunnels that are either fabricated or exist naturally.

Figure 3:
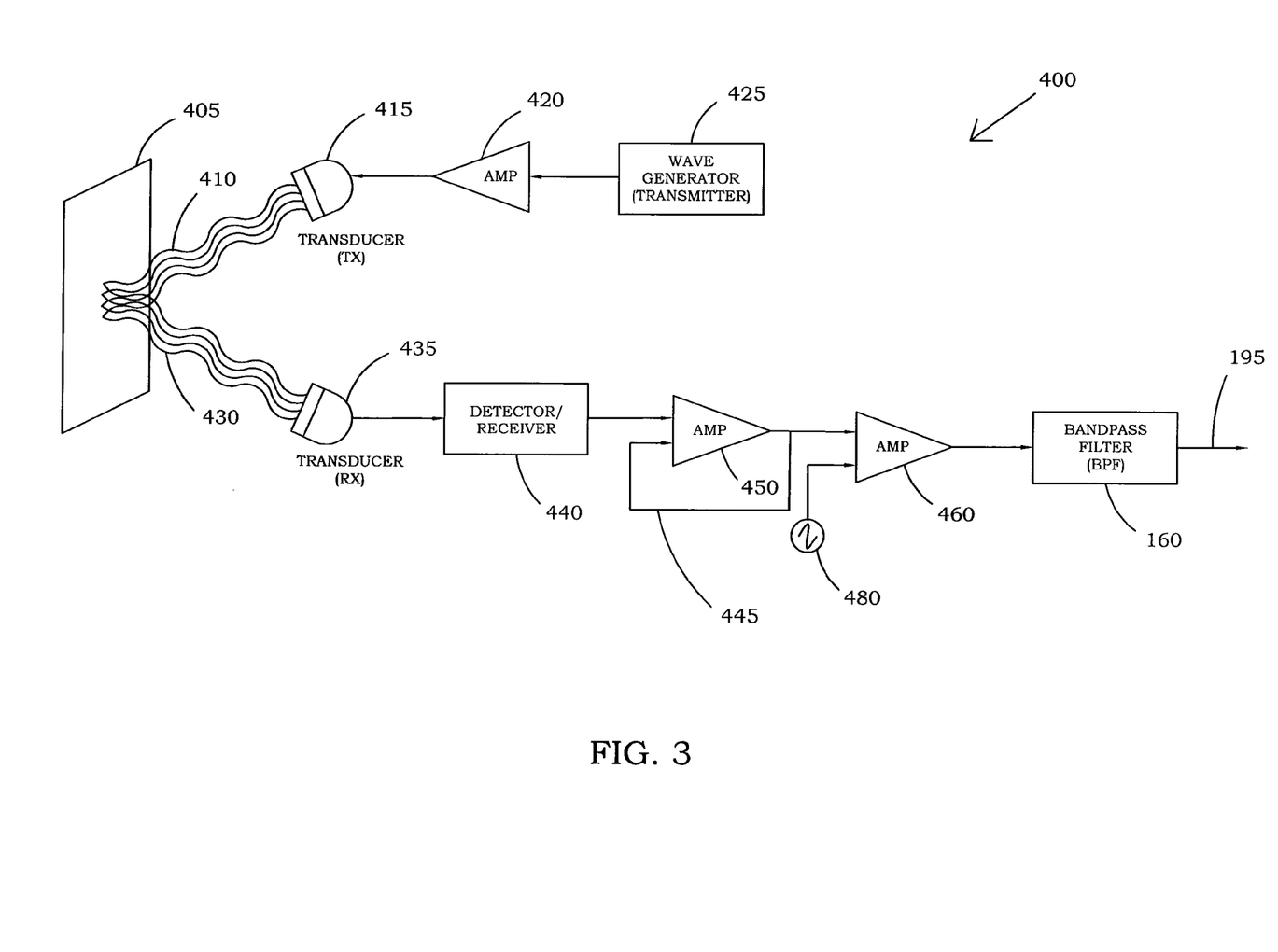
FIG. 3 is a schematic functional block diagram for an ultrasonic transmitter and receiver in accord with one possible embodiment of the present invention.

A more detailed functional block diagram view of ultrasonic sensor 150, signal amplifier 155, and process filter 160 is shown in FIG. 3. One possible embodiment of ultrasonic sensor 150 may comprise wave generator 425, amplifier 420, transducer (TX) 415, transducer (RX) 435, and detector/receiver 440. Wave generator 425 originates an ultrasound signal. The frequency of the signal is preferably adjustable to accommodate whether the system is mobile or not. Generally, higher frequencies are generated when the system is moving. Thus, the system may be adjustable to being mobile or stationary. Amplifier 420 amplifies the signal to permit the signal being used over longer distances. The frequencies of the amplified signal are applied to transducer transmitter 415. On target 10, target area 405 is the particular point or position being scanned with the transmitted ultrasonic signal 410 produced by transducer (TX) 415. In one embodiment, the frequencies from the reflected ultrasonic wave 430 are sensed and transformed to an electrical signal by transducer receiver 435. Detector/Receiver circuitry 440 detects and amplifies this electrical signal. The ultrasonic receiver and processing circuitry may be utilized independently of laser vibrometer sensor 135, if that functionality is desired.

In one possible embodiment, signal amplifier 155 of FIG. 1 may comprise two amplifier circuits 450 and 460. Amplifier 450 receives the unprocessed signal from the detector/receiver 440. In this embodiment, the output of the signal amplifier 450 is provided as feedback 445 into the input of amplifier 450 for stability reasons. The output of signal from amplifier 450 is gain compensated with electronics designed to compensate for the strength of the received signal. Amplifier 450 may also comprise an adjustable/variable gain control. The output signal from amplifier 450 proceeds toward amplifier 460. Amplifier 460 is utilized to convert the compensated signal 445 to a pulse-width modulation (PWM) signal. The two basic components that form this stage comprise frequency carrier waveform 480 and amplifier 460. Amplifier node 460 may also comprise an automatic gain control circuit.

Signal stabilizer/conditioner 111 provides circuitry that removes extra pulses inserted into the video signal due to the dynamic nature of the system. Thus, the video signal is protected against corruption. This means that system vibration, phase shift, noise, aliasing, and other environmental issues that can cause degradation to the captured images can be nullified in order to provide clean video prior to data processing.

Laser 112 can be optionally added for removing environmental noise and vibration from the analyzer 100. Laser 112 can be a laser velocimeter capable of detecting generalized environmental noise from target 10. Laser 112 can also be utilized as a listening device. It can be an infrared laser transmitting and receiving an infrared beam and reflection. This reflection being translated into an audible signal from an intended target. As one possible example, the company Polytec GMBH and others produce this type of laser vibrometer.

High pass filter 114 joined to laser 112 provides an adjustment to the lower cutoff frequency of the input signal. It is expected to block low frequencies, e.g., below 200 Hz. Such disrupted frequencies (noises) are produced by human activity or vehicular traffic, electrical transformers, operating engines, wind, and seismic activities. Those types of noise are unwanted background noise. The amplitude of those signals is preferably reduced by at least above 3 dB, which amounts to about 70.71% of the input signal. High pass filter 114 preserves the high frequency components and allows them to pass the filter. As the frequency increases, the attenuation decreases. This maximizes ultrasonic frequencies.

For simplicity, the filters may be made from passive components rather than active filters. When resistor/capacitor passive components are utilized, then high pass filter 114 and low pass filter 117 may preferably be swapped in location in the functional diagram configuration. However, if inductors replace the capacitors, then the current functional configuration may preferably be utilized. As an alternative, active higher order filters can be used instead of passive filters to provide sharper cut off frequencies.

Preamplifier 116 amplifies the signal that passes through high pass filter 114 to ensure the amplitude is not degraded, and maintains the quality of received audible sound. Low pass filter 117 preserves the low frequencies and eliminates excessively high frequencies from passing.

Activating switch 121 will cause the low pass filter 117 to be by-passed. This may be useful when the noise produced by the subject area under the test is not normal. This situation may occur with high speed winds and the like. Activating switch 122 bypasses high pass filter 114. Switch 121 might be utilized when calm weather conditions prevail or when there are no winds. The integration of high pass filter 114 and low pass filter 117 into laser vibration analyzer 100 creates a wide band pass filter which acts as noise rejection filter outside the upper and lower frequency cutoffs.

Switch 119, buffer 123, amp 124 and headphones 126 provide a system for manually monitoring environmental noise. Buffer 123 is needed to prevent the received audio sound amplitude from being reduced and impeding the input path signal from filter 117 or preamp 116. Switch 119 can be opened or closed based on operator need. Amplifier 124 amplifies the received signal from buffer 123. The gain (dB) can be adjusted as needed. Head phone set 126 permits an operator to listen to the received sound.

Weather sensor 127 is utilized to obtain data and provide readouts for the wind speed, temperature, humidity, and pressure. These readings are recorded by recorder 175 and can be used to modify the collected data. All of these elements can play a significant role in vibrations. Based on readings from weather sensor 127, indicating strong wind conditions, various filtering actions can be performed. Switches 7 and/or 121 may be opened or closed. Activation of switch 7 allows removal of wind induced vibration from digital image output. Buffer 128 is added to the system to avoid signal degradation, which may otherwise occur during the noise rejection procedure. Adder 110 sums signals from signal stabilizer/conditioner 111 and one way switch 7, which can be selectively connected to buffer 128.

Figure 2:
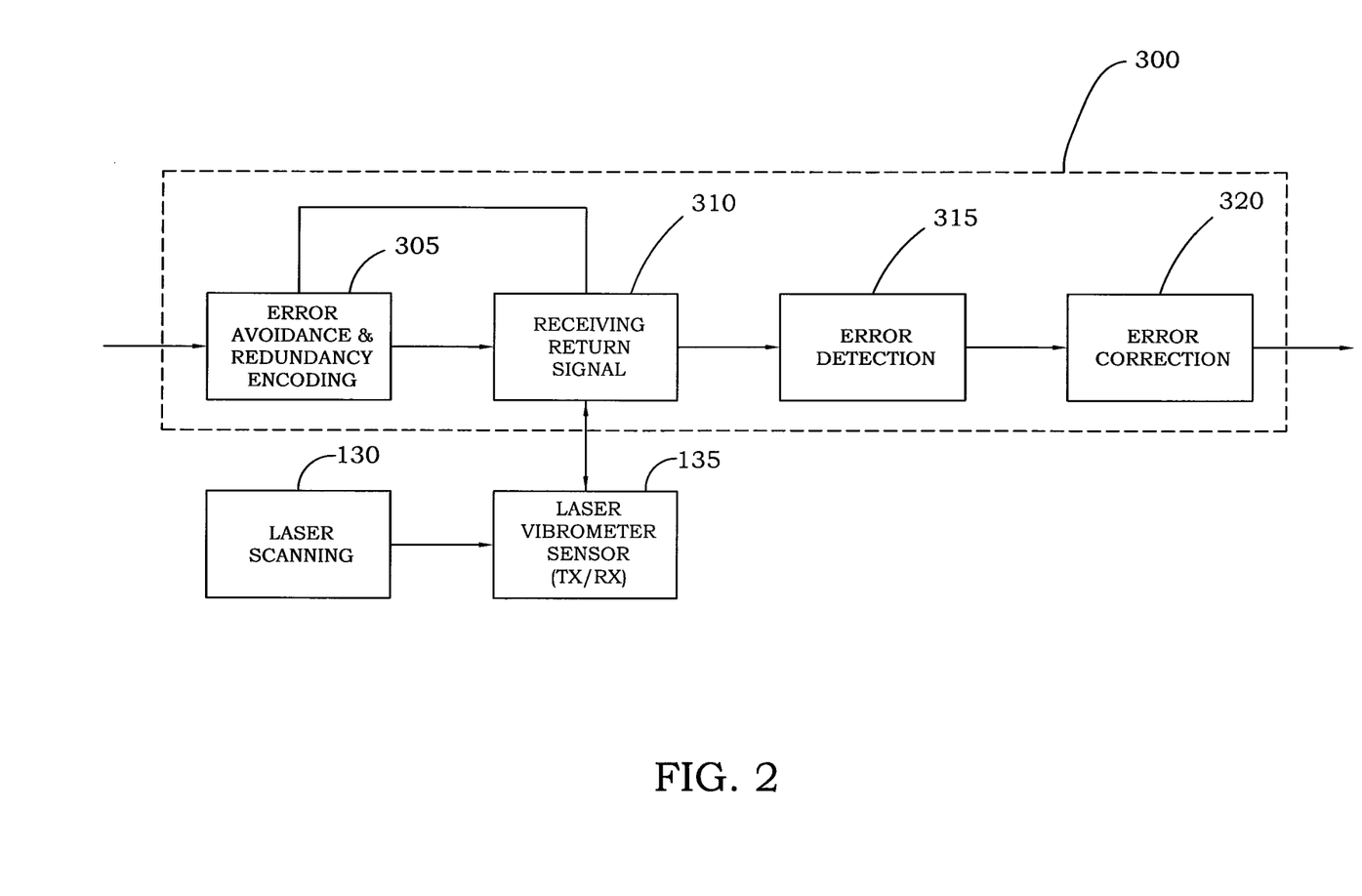
FIG. 2 is a schematic functional block diagram for an error correction circuit in accord with one possible embodiment of the present invention.

Error correction circuit 300, which is shown in more detail in FIG. 2, is utilized to ensure the signal is free of errors so that actual areas of interest that may indicate structural problems found in target 10 are not compromised and that the chance of a false indication is reduced.

Referring now to FIG. 2, there is shown a more detailed view of error correction circuit 300 in FIG. 1. Error correction circuit 300 operates on signals essentially originating from camera 105, laser vibrometer sensor 135 and laser listening device 112. The purpose of error correction circuit 300 is to ensure the signal is free of errors and the signals from real existing detected hot spots or problem spots in target 10 are not compromised.

The collective signals received from the adder 110 and/or laser vibrometer 135 and/or other sources shown in FIG. 1 are processed to ensure errors are avoided using error avoidance and redundancy encoding circuit 305, which is capable of handling the various types of input, e.g., digital images, frequency information, and audio information. Receiving return signal 310 provides an indication whether a suitable signal is received. If not, then laser vibrometer sensor 130 scanning speed can be adjusted.

Error detection circuit 315 detects errors that are encountered by the system and allows the operator to make adjustments in some form such as scanning speed reduction and/or increasing power to laser vibrometer sensor 135. If an error is detected by error detection circuit 315, then error correction circuit 320 corrects these errors.

Processor overlay 115 receives and overlays or merges corrected data from laser vibrometer sensor 135 with the video produced through high resolution camera 105. This results in a data file having X and Y Cartesian coordinates, at least one visual data parameter and a vibration parameter, such as velocity or acceleration. In one possible embodiment, the digital high resolution camera and the laser scan point may be activated utilizing a single switch.

Noise discrimination filter 120 can be operated in accord with the teachings of U.S. Pat. No. 7,277,573, issued to Francis J. O'Brien, Jr., which is incorporated herein by reference. Noise discrimination filter 120 is required in order to process the incoming signals in a timely and efficient manner, and to isolate noise from the real signals and provide an indication that a particular position is an area of concern.

The noise discrimination of U.S. Pat. No. 7,277,573 comprises a multi-stage method that automatically characterizes data sets containing data points, which are each defined by measurements of three variables, as either random or non-random. A three-dimensional Cartesian volume is sized to contain all of a total number N of data points in the data set that is to be characterized. The Cartesian volume is partitioned into equal sized cubes, wherein each cube may or may not contain a data point. A predetermined route is defined for the digital images that goes through every cube or section of the image one time and scores each cube or section as a one or a zero thereby producing a stream of ones and zeros. The number of runs is counted and utilized to provide a Runs Test, which predicts if the N data points in any data set are random or nonrandom. Additional tests are used in conjunction with the Runs Test to increase the accuracy of characterization of each data set as random or nonrandom.

In operation, the coordinates of the position, the visual parameter and the vibration parameter are provided to the noise discrimination routine. The noise discrimination routine can be performed individually on the visual data, the vibration data and a combination of both types of data. The noise discrimination routine will provide a probability of the data being non-random. Non-random data will indicate a discontinuity or defect in the position of interest.

As an alternative to the method of U.S. Pat. No. 7,277,573, the input data can be smoothed using a low-pass filter. Low pass filtering reduces or eliminates contaminating factors, principally environmental/vibration noise caused by moving objects (cars, trucks) and other factors that subject a bridge to stress.

Audio/video preamplifier 125 processes the signal from the noise discrimination filter. Audio/video preamplifier 125 preferably has multiple inputs and outputs capabilities. Audio/video preamplifier 125 can receive a user provided threshold that can be adjusted to highlight non-random data to a tolerance specified by the user. The user can also choose the most significant component of the visual, audio or combined data. The signal gains can be adjusted and are variable.

One-way switch 5 is utilized to record signals from audio/video preamplifier 125 utilizing recording circuitry 175, when desired. Recording circuitry 175 in the system is set to record a long duration of video and audio including the strength of the signal in FFT form that is processed through the ultrasonic components of the system. The FFT form is received from the signal conditioner 170. Audio and video indicate the hot spots received from the audio/video preamplifier 125. Recording circuitry 175 can be operated with one input at a time or with multiple inputs if the equipment allows. In addition, recording circuitry 175 works in conjunction with LCD display with recording node 190 through a USB connector. Y switch 103 is set to CY, or neutral, when replaying captured data recorded from recording circuitry 175.

Y switch 103 is a three way switch. When the switch is set to AY all signals from node 125 are recorded. When the switch is set to CY, the power spectrum, or FFT, for the signal originating from ultrasonic sensor 150 is recorded. When Y switch 103 is set to BY, then Y switch 103 is in a neutral position and in this case recording of new data does not occur. However, this switch position may be used to replay recorded data from recording circuitry 175 and/or record or display the recorded data by inputting the recorded data to the USB connector of LCD display with recording circuitry 190. The display can be operated in two modes. When Y switch 103 is set to BY, LCD display 190 is operable to replay gathered data from either audio/video preamplifier 125 or the power spectrum from the signal conditioner 170. These signal segments may be displayed in spectrogram form so as to easily permit visualization of any detected hot spots. Both of these signals are passed to the LCD display via Y switch 103.

Recording capability is also embedded into the LCD display with recording circuitry. The estimated time of recording may exceed eight hours. In addition, the recorded data can be transferred to an external hard drive through the USB connector. This USB recording capability may be added to the system as a backup, which also can be used to extend the recording hours for the system. Data from audio/video 125 and signal conditioner 170 can be recorded.

In one embodiment of this invention, a user can observe the data in real time as camera 105 and scanning laser 130 are receiving data from the laser vibration analyzer. Preamplifier 125 can be adjusted to alert the user to areas of interest. In another embodiment recording circuitry 175 can be used to record the system data including the preamplifier 125 output.

Scale adjustment 185 can be utilized to zoom the displayed information in or out. This can be used to help the technician understand and clear up complicated signals. In addition, scale adjustment 185 can be used to add some type of measurement to trouble areas that were originally processed through audio/video preamplifier 125. The x and y axis from an FFT can be scaled showing amplitude versus frequency.

Speaker 107 is utilized to play back sounds that may be created during the vibration examination utilizing laser 112.

Bandpass filter 160, shown also in FIG. 1 as process filter 160, may have a manual and/or an automatic adjustment of the passband. The automatic adjustment may be based on the frequency that is initially applied to transducer TX 415 by wave generator 425. Referring again to FIG. 1, two-way switch 6 selectively connects output 195 from bandpass filter 160 to recording circuit 175.

Analog to digital converter 165 processes output signal 195 by converting the signal from analog to digital. Analog to digital converter 165 preferably utilizes at least a 16 bit conversion. Signal conditioner 170 performs a fast Fourier transform (FFT) for the signal from analog to digital converter 165.

In summary of operation of laser analyzer 100, ultrasonic sensor 150 scans an ultrasonic signal along target 10. The scan is coordinated with the scanning of laser vibrometer sensor 135, which detects variations in the laser signal that may show resonance, discontinuities, or the like, which indicate structural defects. Camera 105 is also coordinated in the scanning and records a visual indication, which is then combined with the signal from laser vibrometer sensor 135. Laser 112 may be utilized to produce a corresponding acoustic signal, which may be added to this signal by adder 110. Laser 112 may also be coordinated in the scanning so that camera 105, laser vibrometer sensor 135, ultrasonic sensor 150, and laser 112 are aimed at the same locations to provide matching data for the data points so created.

The signals may be recorded and/or displayed by LCD display with recording circuitry 190. The data may be displayed in color, which illustrates the vibrational signal ranges on the digital image. Certain spectrogram colors may be utilized to show regions with potential defects. The digital signal may also include information such as latitude and longitude of the target for use for quickly providing a map showing bridges or other targeted structures with unacceptable levels of potential defects.

Accordingly, the present inventive method provides a laser measurement tool dependent on an ultrasonic operator that would measure vibrations of locations of interest on a solid structure. The device will be able to detect hot spots resulting from some types of vibrations and empty or semi-empty gaps that otherwise cannot be recognized by observation, visualized, or felt. The laser scanning device detects abnormalities in the structure through feedback caused by the ultrasonic sensor 150. The scanned area is filmed and filtered and may be analyzed through a digital signal processing system aimed to pinpoint the vulnerable spots that are located on the targets of interest. The degree of vibrations can be analyzed immediately, perhaps in color, and/or electronically pointed out, without requiring theoretical interpretation.

For these reasons, the present proposes a unique way to streamline data collection and analysis by means of a novel three-dimensional spatial randomness assessment tool.

Application of this tool and pre-processing filtering steps assures the probable success of the method applied to the task. In essence, the noise discrimination tool, as well as other significant enhancements described hereinbefore, assures that the integrity of the diagnostic system is not compromised by the presence of vibrations, background noise, traffic noise, transformer noise, engine (machinery) noise, seismic noise, and other interferences inherent in the large-sample task carried out in the dynamic environment of nature. Due to the noise reduction, the present invention may operate from distances up to 300 meters and even beyond 300 meters under good weather conditions.

Many additional changes in the details, components, steps, and organization of the system, herein described and illustrated to explain the nature of the invention, may be made by those skilled in the art within the principle and scope of the invention. It is therefore understood that within the scope of the appended claims, the invention may be practiced otherwise than as specifically described.

What is claimed is:

1. A method for locating defects in a target comprising the steps of:
   transmitting an ultrasonic signal to said target;
   transmitting a first laser beam to said target at a known position on said target;
   receiving a first reflection of said first laser beam;
   producing a vibration signal from said first reflection of said first laser beam responsive to vibrations produced in said target by said ultrasonic signal;
   transmitting a second laser beam to said target;
   receiving a second reflection of said second laser beam;
   determining an environmental vibration signal from said received second reflection;
   utilizing said determined environmental vibration signal to remove the effect of environmental vibrations from said produced vibration signal;
   producing digital images of said target at a region including the known position on the target;
   overlaying said digital images with said vibration signal with environmental vibrations removed to provide data points of overlaid data;
   utilizing a runs test for determining a probability of said overlaid data being non-random data points;
   selecting a threshold probability of said overlaid data being non-random data points; and
   indicating a potential area of concern for inspection where said overlaid data has a probability above a selected threshold of being non-random data points.

2. The method of claim 1 further comprising the step of utilizing said determined environmental vibration signal to remove the effect of environmental vibrations from said digital images.

3. The method of claim 1 further comprising the steps of:
collecting wind speed data about said target; and
utilizing said wind speed data to control said step of utilizing said determined environmental vibration signal.

4. The method of claim 1 wherein said determined environmental vibration signal is provided to a user as an audio signal.

* * * * *